United States Patent
Kim et al.

(10) Patent No.: US 7,635,331 B2
(45) Date of Patent: Dec. 22, 2009

(54) NON-INVASIVE BLOOD GLUCOSE SENSORS USING A MAGNETO-RESONANCE ABSORPTION METHOD AND MEASUREMENT METHODS THEREOF

(75) Inventors: Dong-kyun Kim, Suwon-si (KR); Jong-hwa Won, Suwon-si (KR); Evgeny Alexandrovich Protasov, Moscow (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 639 days.

(21) Appl. No.: 11/177,351

(22) Filed: Jul. 11, 2005

(65) Prior Publication Data
US 2006/0020193 A1 Jan. 26, 2006

(30) Foreign Application Priority Data
Jul. 9, 2004 (KR) .................. 10-2004-0053575

(51) Int. Cl.
*A61B 5/00* (2006.01)
*A61B 5/05* (2006.01)
*G01V 3/00* (2006.01)

(52) U.S. Cl. .................. 600/365; 600/347; 324/307
(58) Field of Classification Search .............. 600/345, 600/347, 348, 365; 324/307, 311
See application file for complete search history.

(56) References Cited

U.S. PATENT DOCUMENTS 4,875,486 A 10/1989 Rapoport
4,994,746 A 2/1991 Panosh (Continued)

FOREIGN PATENT DOCUMENTS

JP 06-148304 5/1989

(Continued)

OTHER PUBLICATIONS

James Keeler, Understanding NMR Spectroscopy, "NMR and Energy Levels," Chapter 2, 2002.*

(Continued)

*Primary Examiner*—Charles A Marmor, II
*Assistant Examiner*—Christian Y Jang
(74) *Attorney, Agent, or Firm*—Sughrue Mion, PLLC

(57) ABSTRACT

A non-invasive blood glucose measurement method using a magneto-resonance absorption method. A constant magnetic field is applied using a pair of permanent magnets, the magnetic field having a uniform strength. A triangular waveform low frequency modulation magnetic field is applied using a low frequency generator and a pair of low frequency coils, the low frequency modulation magnetic field having a uniform strength. A weak acoustic wave modulation magnetic field is applied using an acoustic wave generator and a pair of acoustic wave coils. Electromagnetic waves are applied to a detector in which a finger is positioned to produce a nuclear magneto-resonance, the electromagnetic waves having a frequency varying in a specific frequency band step by step, the applying being done using a high frequency generator and a sensor coil. A magneto-resonance absorption signal produced by spin-lattice relaxation of protons in a tissue of the finger because of the nuclear magneto-resonance is detected. A magneto-resonance spin-lattice relaxation time of the finger from the magneto-resonance absorption signal is determined. A blood glucose concentration in a human body is determined from a correlation between a pre-determined blood glucose concentration in the human body and the determined magneto-resonance spin-lattice relaxation time.

36 Claims, 6 Drawing Sheets

U.S. PATENT DOCUMENTS

| | | | |
|---|---|---|---|
| 5,619,139 A * | 4/1997 | Holczer et al. | 324/318 |
| 5,685,300 A | 11/1997 | Kuenstner | |
| 5,921,928 A * | 7/1999 | Greenleaf et al. | 600/437 |
| 5,952,734 A * | 9/1999 | Gelbien | 307/91 |
| 6,163,154 A | 12/2000 | Anderson | |
| 6,404,197 B1 * | 6/2002 | Anderson et al. | 324/311 |

FOREIGN PATENT DOCUMENTS

| | | |
|---|---|---|
| JP | 05-502097 A | 4/1993 |
| JP | 01-119746 | 5/1994 |

OTHER PUBLICATIONS

Japanese Patent Office Action issued Jun. 17, 2008 with certification statement.

\* cited by examiner

NON-INVASIVE BLOOD GLUCOSE SENSORS USING A MAGNETO-RESONANCE ABSORPTION METHOD AND MEASUREMENT METHODS THEREOF

REFERENCE TO RELATED APPLICATIONS

This application claims the benefit of Korean Patent Application No. 2004-53575, filed on Jul. 9, 2004, in the Korean Intellectual Property Office, the disclosure of which is incorporated herein by reference.

BACKGROUND OF THE INVENTION

1. Field of the Invention

The present invention relates to an apparatus and method for non-invasively measuring a blood glucose concentration in the human body, and more particularly, to a non-invasive blood glucose sensors using a magneto-resonance absorption method and measurement methods thereof.

2. Description of the Related Art

Diabetics have suddenly increased in number due to lack of physical activities and changes of eating habits. The deaths caused by diabetes in 2001 in Korea are 23.8 people per hundred thousand people, stand fourth in the death causes, and increased about two times 11.8 people per hundred thousand people in 1990. Individual diabetics must measure blood glucose by themselves due to the increase in number, i.e., self-monitoring of blood glucose is required. Self-monitoring of blood glucose is an important component of modern therapy for diabetes and offers information about blood glucose levels at many times points to enable maintenance of a more constant glucose levels in everyday life. The self-monitoring of blood glucose is suggested to be taken at least three or four times a day. However, it is reported that only 18% of diabetics periodically measure blood glucose even in the U.S.A in a good social welfare. The negligence of the measurement of blood glucose is due to current invasive-type glucose meters which require blood samples directly taken from the body. Periodical tests by the invasive method not only give pain or uncomfortable feelings during taking bloods but also impose mental and economic burdens with considerable costs of consumable accessories necessary for taking bloods.

Devices for non-invasive measurement of blood glucose have been developed to solve such pain and displeasure during taking of blood, to reduce cost of diagnostic strips and to smoothly perform self-measurement of the blood glucose. As non-invasive measurement methods of blood glucose, methods of using an analysis of a absorption spectrum in an infrared zone and a method of using impedance spectroscopy in a band of tens to hundreds MHz have been studied.

Also, non-invasive blood glucose measurement methods using a nuclear magneto-resonance spectroscopy principle are disclosed in U.S. Pat. Nos. 4,875,486, 5,685,300, and 6,163,154. In such measurement methods, a correlation between a resonance peak (or area) by a water component and a resonance peak (or area) by a glucose component on a nuclear magneto-resonance spectrum of blood or the tissue of the human body is used or a degree of a chemical shift by the glucose component on the spectrum is used to measure blood glucose, the chemical shift being caused by variations in a blood glucose concentration. However, due to the effect of the nuclear magneto-resonance spectrum by the water component, it is substantially very difficult to sense a variation in the magnitude of the resonance peak or a very small variation in the chemical shift by the glucose component. Thus, non-invasive blood glucose sensors using such measurement methods are not developed yet.

There is reported a magneto-resonance absorption method (O. C. Esicov and E. A. Protasov, "Magneto-resonance method of measurement of spin-lattice time by using absorption signal," Scientific session MEPhI Conference, Vol. 4, pp. 35, 2003.) by which an absorption signal in a time domain occurring during nuclear magneto-resonance is measured to analyze components in a material. There is reported a glucose concentration measurement method using an electromagnetic field (E. A. Protasov, O. C. Esicov and E. C. Karpova, "Glucose concentration measurements in the human blood by NMR method," Scientific session MEPhI Conference, Vol. 5, pp. 3, 2003) by which a correlation between a blood glucose level in blood or the human body and a magneto-resonance spin-lattice relaxation time measured by a magneto-resonance absorption method is defined to determine a blood glucose concentration in blood or the human body using the correlation.

An external magnetic field must be highly uniform in order to secure the measurement precision in blood glucose measurement using a nuclear magneto-resonance principle. However, the essential uniformity of the external magnetic field may not be secured in existing blood glucose sensors using an electromagnetic field due to the unstableness of a supplied voltage. Thus, it is unreasonable that the existing blood glucose sensors are commonly used. For reference, according to the existing blood glucose measurement results, the uniformity of an external magnetic field having the strength between 0.15 T and 0.35 T must be within a range of $2.5 \times 10^{-4}$ T to detect variations in a spin-lattice relaxation time of a finger or a blood sample caused by variations in a blood glucose concentration. Also, blood glucose sensors using an electromagnetic field are constructed considerably heavy and big in order to form an external magnetic field having a desired strength and thus are not suitable as home non-invasive blood glucose sensors.

Russian Pat. No. 33235 discloses a non-invasive blood glucose sensor using permanent magnets to non-invasively measure blood glucose using a magneto-resonance absorption method. In this non-invasive blood glucose sensor, a pair of permanent magnets is used to form a constant magnetic field so as to remove variations in the magnetic field caused by an unstable power supply. However, it is difficult to obtain the required uniformity of the magnetic field with only the pair of permanent magnets. The uniformity of the magnetic field basically depends on the perfection of the permanent magnets. Thus, the irregular arrangement of foreign bodies, bubbles, or contents in a material of the magnets causes a disturbance of local magnetization, the disturbance distorting the magnetic field. The non-invasive blood glucose sensor is a single closed shell, internal elements of which are connected to form a magnetic circuit. Since the accurate arrangement of the internal elements of the shell is difficult due to the single closed structure, the internal elements are disarranged. Thus, the distribution of the magnetic field is non-uniform. Absorption pulses of a detected signal are distorted or diffused by the non-uniform distribution of the magnetic field. Thus, it is difficult to accurately detect an absorption signal and measure a nuclear magneto-resonance spin-lattice relaxation time. As a result, the precision or accuracy of the determination of a blood glucose level in the human body is deteriorated.

SUMMARY OF THE INVENTION

Accordingly, the present general inventive concept has been made to solve the above-mentioned and/or problems, and an aspect of the present general inventive concept is to provide a non-invasive blood glucose sensor using a magneto-resonance absorption method which does not require pricking for blood sample, by which users can precisely and accurately perform periodic self-measurement of blood glucose in their homes and a measurement method thereof.

According to an aspect of the present invention, there is provided a non-invasive blood glucose sensor using a magneto-resonance absorption method, including: a measuring unit forming a plurality of magnetic fields for measuring a spin-lattice relaxation time of protons in a tissue of a finger, applying electromagnetic waves, and detecting a nuclear magneto-resonance absorption signal using the magneto-resonance absorption method; and a circuit unit generating the electromagnetic waves necessary for the measuring unit and determining the spin-lattice relaxation time of the protons in the finger tissue and a blood glucose concentration in the human body from the nuclear magneto-resonance absorption signal.

The measuring unit may include: a detector fixing the finger to measure the spin-lattice relaxation time of the protons in the finger tissue; a sensor coil applying electromagnetic waves having a frequency producing a nuclear magneto-resonance to the detector and measuring the nuclear magneto-resonance absorption signal; a pair of permanent magnets applying a uniform constant magnetic field to the detector; a pair of pole pieces improving a uniformity of the constant magnetic field applied to the detector; a pair of low frequency coils applying a low frequency modulation magnetic field to the detector; a pair of acoustic wave coils applying an acoustic wave modulation magnetic field to the detector so as to easily detect a weak absorption signal; a shield comprising the detector and the sensor coil and coupling the detector and the sensor coil to the pair of pole pieces; and a cylindrical shell coupling the elements to form a magnetic circuit and performing magnetic shielding.

Here, the pair of permanent magnets may be cylindrical and disposed so that opposite magnetic poles face each other, and the pair pole pieces may also be cylindrical and respectively installed inside the pair of permanent magnets so as to have the same rotation axes as the pair of permanent magnets. The detector may have a cylindrical shape, a side of which is stopped, and the sensor coil may be wound in a circumferential direction of the detector. The shield may be installed between the pair of pole pieces so that a rotation axis of the detector is perpendicular to the rotation axes of the pair of permanent magnets and the pair of pole pieces. The pair of low frequency coils may be wound in a circumferential direction of the pair of permanent magnets, and the pair of acoustic wave coils may be wound in a circumferential direction inside the pair of pole pieces.

The shell may have a rotation axis coinciding with the rotation axis of the detector and an inner wall protruding inside to be structurally coupled to outer sides of the pair of permanent magnets. Protection plates may be attached to both ends of the shell to protect elements installed inside the shell. An insertion hole through which a finger is inserted into the shell and a hole electrically coupling the coils to the circuit unit may be formed in the center of the protection plates.

The circuit unit may include: a high frequency generator generating electromagnetic waves having a frequency producing a nuclear magneto-resonance and detecting a magneto-resonance absorption signal; a low frequency generator generating electromagnetic waves for applying a low frequency modulation magnetic field to the detector together with the pair of low frequency coils; an acoustic wave generator generating acoustic waves for applying an acoustic wave modulation magnetic field to the detector together with the pair of acoustic wave coils; an amplitude detector measuring an amplitude of the detected weak absorption signal; a preamplifier amplifying the weak absorption signal; an acoustic wave amplifier amplifying an acoustic wave band component of the absorption signal; a band pass filter selectively detecting only the acoustic wave band component of the absorption signal; a calculating unit determining the spin-lattice relaxation time of the protons in the finger and the blood glucose concentration in the human body from the absorption signal comprising the acoustic wave band component; and a drive controller controlling operations of the elements.

Here, the high frequency generator may be a positive feedback amplifier and coupled to the sensor coil, the low frequency generator may be coupled to the pair of low frequency coils, and the acoustic wave generator may be coupled to the pair of acoustic wave coils.

The circuit unit may further include: an amplitude stabilizer stabilizing the amplitude measured by the amplitude measurer and transmitting the stabilized amplitude to the drive controller; a gain controller controlling a gain of the band pass filter; and a display displaying the blood glucose concentration determined by the calculating unit to a user. Amplitudes and time differences of pairs of absorption pulses of the nuclear magneto-resonance absorption signal having passed through the band pass filter may be measured by the calculating unit or by an additional measurer installed in front of the calculating unit. The drive controller and the calculating unit may be embodied as programs inside microprocessors or personal computers.

The shell may include a cylinder part including a same rotation axis to rotation axes of the pair of permanent magnets and the pair of pole pieces and a pair of plungers disposed at outer sides of the pair of permanent magnets, so as to easily assemble and disassemble the measuring unit and arrange internal elements. An insertion hole through which a finger is inserted into the shell and a hole electrically coupling internal coils to the circuit unit may be formed in the center of the cylinder part.

According to another aspect of the present invention, there is provided a non-invasive blood glucose measurement method using a magneto-resonance absorption method, including: applying a constant magnetic field having a uniform strength using a pair of permanent magnets; applying a triangular waveform low frequency modulation magnetic field having a uniform strength and cycle using a low frequency generator and a pair of low frequency coils; applying an acoustic wave modulation magnetic field using an acoustic wave generator and a pair of acoustic wave coils; applying electromagnetic waves having a frequency varying in a specific frequency band step by step using a high frequency generator and a sensor coil; generating a magneto-resonance absorption signal by reacting protons in a finger tissue due to the magnetic fields and electromagnetic waves applied by the high frequency generator and the sensor coil; measuring an amplitude of a nuclear magneto-resonance absorption signal using an amplitude measurer; amplifying the weak absorption signal using a pre-amplifier; amplifying acoustic wave band components of the absorption signal using an acoustic wave amplifier; detecting only the acoustic wave band components of the absorption signal using a band pass filter; recording amplitudes and time differences of pairs of absorption pulses; measuring a spin-lattice relaxation time of the protons in the finger tissue from the amplitudes and the time differences of the pairs of absorption pulses; determining a blood glucose concentration in the body from a determined nuclear magneto-resonance spin-lattice relaxation time.

A time required for modulating the triangular waveform low frequency may be more than 10 times the nuclear magneto-resonance spin-lattice relaxation time of the protons in the finger tissue. A time when a frequency of electromagnetic waves generated by the high frequency generator varies may synchronize with a time when the low frequency modulation magnetic field is minimum. Also, a pair of absorption pulses may be recorded from the nuclear magneto-resonance absorption signal in each cycle of the triangular waveform low frequency modulation magnetic field. A time difference between a pair of absorption pulses must be smaller than the spin-lattice relaxation time of the protons. The blood glucose concentration in the body may be determined through a correlation between a blood glucose concentration of an individual obtained through several pre-measurements prior to a substantial measurement and the measured spin-lattice relaxation time.

According to still another aspect of the present invention, there is provided a non-invasive blood glucose measurement method using a magneto-resonance absorption method, including: applying a constant magnetic field having a uniform strength using a pair of permanent magnets; applying an asymmetric low frequency modulation magnetic field using a low frequency generator and a pair of low frequency coils; applying an acoustic wave modulation magnetic field using an acoustic wave generator and a pair of acoustic wave coils; applying electromagnetic waves having a uniform frequency using a high frequency generator and a sensor coil; generating a magneto-resonance absorption signal by reacting protons in a finger tissue due to the magnetic fields and electromagnetic waves applied by the high frequency generator and the sensor coil; measuring an amplitude of a nuclear magneto-resonance absorption signal using an amplitude measurer; amplifying the weak absorption signal using a pre-amplifier; amplifying acoustic wave band components of the absorption signal using an acoustic wave amplifier; detecting only the acoustic wave band components of the absorption signal using a band pass filter; recording amplitudes and time differences of pairs of absorption pulses; measuring a spin-lattice relaxation time of the protons in the finger tissue from the amplitudes and the time differences of the pairs of absorption pulses; determining a blood glucose concentration in the body from a determined nuclear magneto-resonance spin-lattice relaxation time.

The asymmetric low frequency modulation magnetic field may include a triangular waveform modulation magnetic field having a uniform strength and cycle and a stepped modulation magnetic field varying in a uniform strength and cycle step by step. A time required for the triangular waveform low frequency modulation may be at least more than 10 times a nuclear magneto-resonance spin-lattice relaxation time of the protons in the finger tissue, and a time for the stepped low frequency modulation may be integer times the triangular waveform low frequency modulation. Also, a pair of absorption pulses of a nuclear magneto-resonance absorption signal may be recorded in each cycle of the triangular waveform low frequency magnetic field modulation. A time difference between the pair of absorption pulses must be smaller than the nuclear magneto-resonance relaxation time of the protons.

According to yet another aspect of the present invention, there is provided a non-invasive blood glucose measurement method using a magneto-resonance absorption method, including: applying a constant magnetic field having a uniform strength using a pair of permanent magnets; applying an impulse type low frequency modulation magnetic field using a low frequency generator and a pair of low frequency coils; applying an acoustic wave modulation magnetic field using an acoustic wave generator and a pair of acoustic wave coils; applying electromagnetic waves having a uniform frequency using a high frequency generator and a sensor coil; generating a magneto-resonance absorption signal by reacting protons in a finger tissue due to the magnetic fields and electromagnetic waves applied by the high frequency generator and the sensor coil; measuring an amplitude of a nuclear magneto-resonance absorption signal using an amplitude measurer; amplifying the weak absorption signal using a pre-amplifier; amplifying acoustic wave band components of the absorption signal using an acoustic wave amplifier; detecting only the acoustic wave band components of the absorption signal using a band pass filter; recording amplitudes and time differences of pairs of absorption pulses; measuring a spin-lattice relaxation time of the protons in the finger tissue from the amplitudes and the time differences of the pairs of absorption pulses; determining a blood glucose concentration in the body from a determined nuclear magneto-resonance spin-lattice relaxation time.

A cycle of the impulse type low frequency modulation magnetic field may be at least more than 10 times a nuclear magneto-resonance spin-lattice relaxation time of the protons in the finger tissue, and a lasting time of the impulse may increase in each cycle of low frequency modulation step by step. An amplitude of the impulse may be greater than a difference between a strength of magnetic field corresponding to a resonance frequency of electromagnetic waves applied by the high frequency generator and a strength of the constant magnetic field so as to detect a pair of absorption pulses in each cycle of low frequency modulation.

The above-described non-invasive blood glucose sensor can secure the required uniformity of a magnetic field and improve the precision and accuracy of blood glucose concentration measurement.

BRIEF DESCRIPTION OF THE DRAWINGS

The above aspects and features of the present invention will be more apparent by describing certain embodiments of the present invention with reference to the accompanying drawings, in which.

DETAILED DESCRIPTION OF THE PREFERRED EMBODIMENTS

Figure 1:
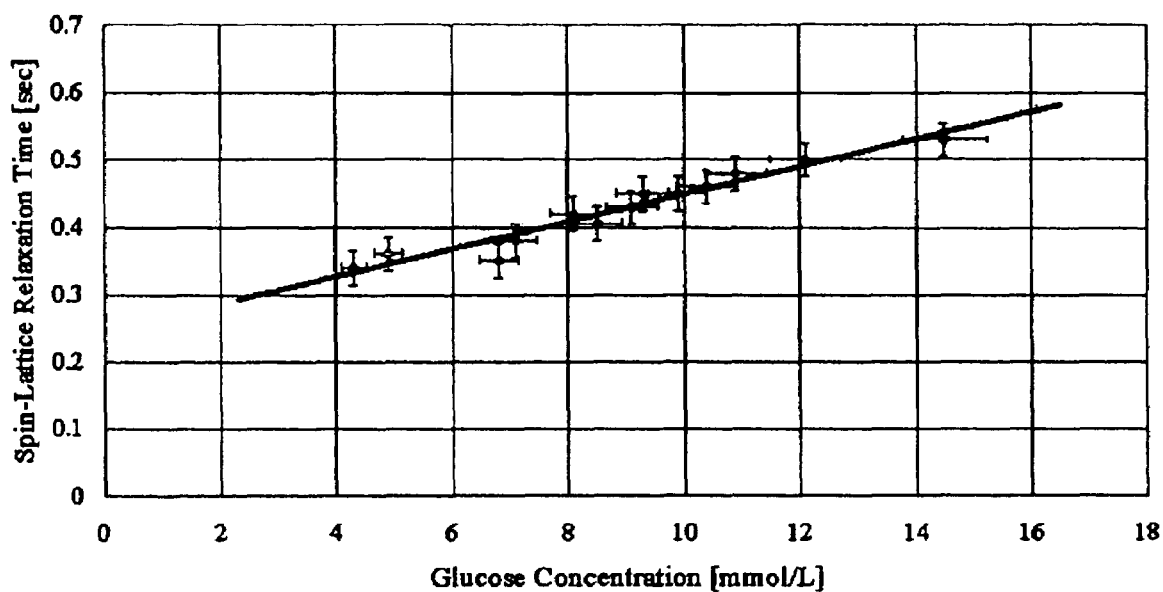
FIG. 1 is a view illustrating experimental data showing a correlation between a blood glucose concentration measured in the human body and a nuclear magneto-resonance spin-lattice relaxation time measured in a finger tissue.

Certain embodiments of the present invention will be described in greater detail with reference to the accompanying drawings.

In the following description, same drawing reference numerals are used for the same elements even in different drawings. The matters defined in the description such as a detailed construction and elements are nothing but the ones provided to assist in a comprehensive understanding of the invention. Thus, it is apparent that the present invention can be carried out without those defined matters. Also, well-known functions or constructions are not described in detail since they would obscure the invention in unnecessary detail.

According to a blood glucose measurement principle of the present invention, a blood glucose concentration in the human body is in direct proportion to a nuclear magneto-resonance spin-lattice relaxation time $T_1$ of the human body, in particular, a finger. FIG. 1 is a view illustrating experimental data showing a correlation between a blood glucose concentration measured in the human body and a nuclear magneto-resonance spin-lattice relaxation time measured in a finger tissue. As shown in FIG. 1, a spin-lattice relaxation time $T_1$ measured in a finger is in direct proportion to a blood glucose concentration measured in the human body. This direct proportion may show a slight difference in individuals. Thus, measurement must be performed several times to find a correlation suitable for a user at a preliminary stage. It is known that a blood glucose concentration and a spin-lattice relaxation time of a gathered blood sample are in direct proportion to each other. Thus, the blood glucose concentration may be measured from the gathered blood sample using this direct proportion relation.

In such a measurement, a finger is an ideal object to be measured. There are numerous capillaries at the end of a finger. A blood speed in the capillaries is within a range between 0.5 and 1.2 mm/s and thus is hardly affected by a blood flow. Also, the volume of interstitial fluid, blood, and muscular tissue occupying the finger is sufficiently larger than the volume of the bone occupying the finger. Thus, amplitude of an absorption signal is sufficiently large and may be easily amplified and processed. Glucose concentrations in the interstitial fluid and the blood are the same. If the bone does not include free protons, a signal is not generated from the bone of the finger. Since a spin-lattice relaxation time of the muscular tissue is relatively short, i.e., about 0.05 seconds, variations in spin-lattice relaxation times of the tissues of all fingers caused by a slight difference in the muscular tissue of each individual are sufficiently low. Therefore, when magneto-resonance absorption signals are measured from the tissues of the fingers, signals are measured only from interstitial fluid and blood components. According to a correlation between the spin-lattice relaxation time and the blood glucose concentration shown in FIG. 1, variations in the spin-lattice relaxation time indicate variation degrees of the blood glucose concentration in the human body.

Figure 2:
FIG. 2 is a view illustrating measurement data of a nuclear magneto-resonance absorption signal according to the prior art.

A nuclear magneto-resonance spin-lattice relaxation time is measured using a magneto-resonance absorption method. The magneto-resonance absorption method is to measure an absorption signal in a time domain occurring during a magneto-resonance so as to analyze components in a material. Protons having weak energy in the tissue of a finger are arranged in the same direction as an external magnetic field and do spinning and precession at a frequency as in Equation 1:

$$\omega_0 = 2\pi v = \gamma_p B \qquad (1)$$

wherein $\omega_o$ denotes a frequency of the precession called a Larmor precession frequency, $B_o$ denotes a strength of an external magnetic field, and $\gamma_p$ denotes a gyromagnetic ratio of the protons which is 42.58 MHz/T. Here, if an electromagnetic wave having the same frequency as the precession frequency is applied to the protons, the protons are excited to a high energy state. Thus, a direction of magnetization is changed into an opposite direction to that of an applied external magnetic field. After a predetermined period, the excited protons emit thermal energy to the outside and then return to their original state. This is called a spin-lattice relaxation phenomenon. Here, an absorption signal is generated at a surrounding induction coil depending on a magnetization direction of the protons. FIG. 2 is a view illustrating measurement data of a nuclear magneto-resonance absorption signal according to the prior art. As shown in FIG. 2, amplitudes of absorption pulses are differently measured depending on time intervals at which nuclear magneto-resonance occurs. In other words, if a time interval at which absorption pulses are generated is sufficiently longer than a spin-lattice relaxation time, absorption pulses having the same amplitude with a uniform magnitude are generated. However, if the time interval at which absorption pulses are generated is shorter than the spin-lattice relaxation time, amplitudes of subsequently generated absorption pulses are relatively small depending on a degree of spin-lattice relaxation and increase as the time interval becomes longer. Also, a noise component is large. The large noise component is generated due to the non-uniformity of an external magnetic field. In this case, a signal to noise ratio (SNR) is about 10.

Figure 3:
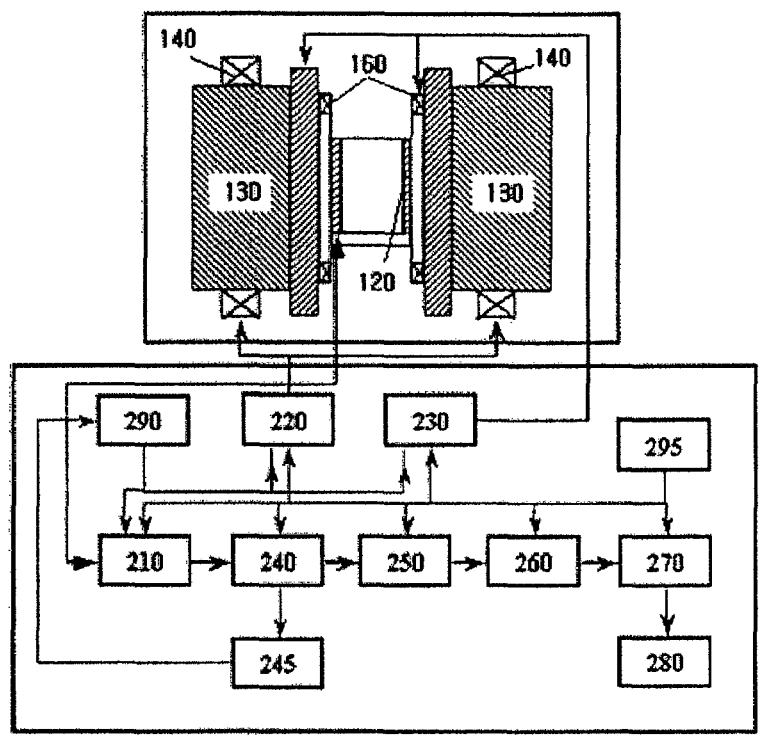
FIG. 3 is a view illustrating a non-invasive blood glucose sensor using a magneto-absorption resonance method according to an embodiment of the present invention.
Figure 4:
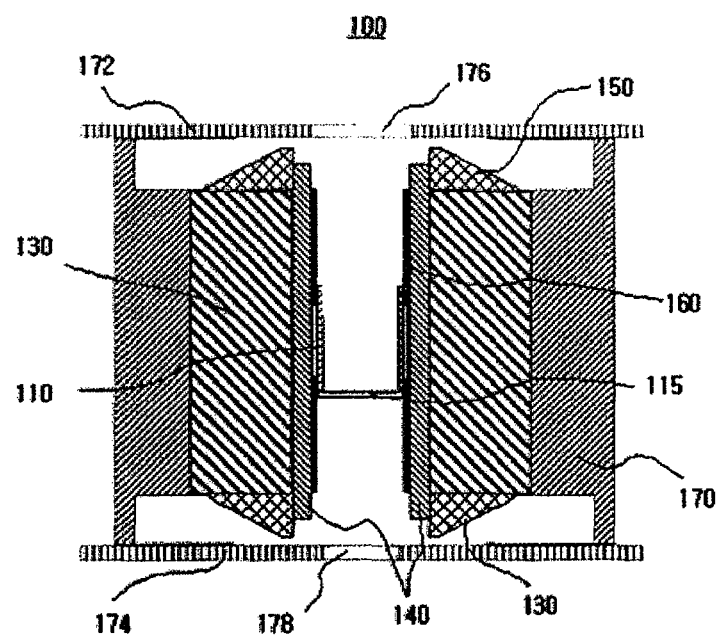
FIG. 4 is a vertical cross-sectional view of a measuring unit of the non-invasive blood glucose sensor shown in FIG. 3.
Figure 5:
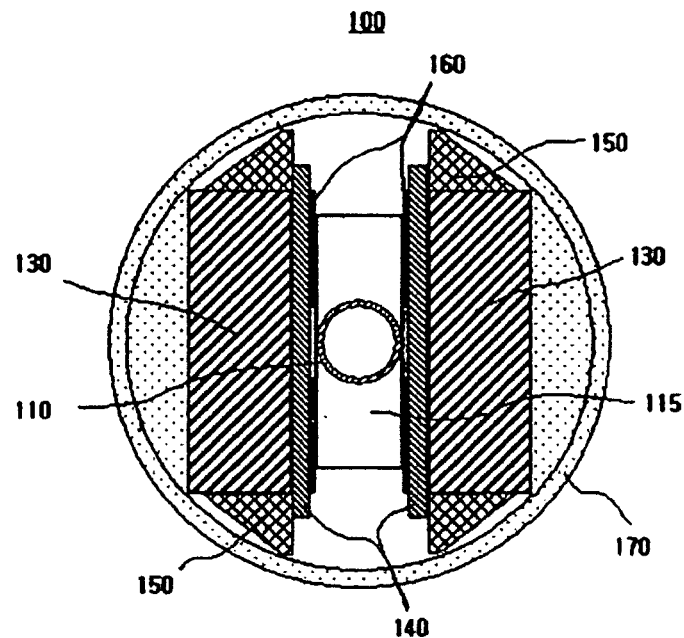
FIG. 5 is a horizontal cross-sectional view of the measuring unit of the non-invasive blood glucose sensor shown in FIG. 3.

FIG. 3 is a view illustrating a non-invasive blood glucose sensor using a magneto-resonance absorption method according to an embodiment of the present invention. FIGS. 4 and 5 are vertical and horizontal cross-sectional views of a measuring unit 100 of the non-invasive blood glucose sensor shown in FIG. 3. The non-invasive blood glucose sensor includes the measuring unit 100 and a circuit unit 200. The measuring unit 100 forms a plurality of magnetic fields for measuring a spin-lattice relaxation time $T_1$ of protons in a tissue of a finger using a magneto-resonance absorption method and applies electromagnetic waves to detect a nuclear magneto-resonance absorption signal. The circuit unit 200 generates the electromagnetic waves for the measuring unit 100 and determines the spin-lattice relaxation time $T_1$ of the protons in the tissue of the finger and a blood glucose concentration in the human body from the detected nuclear magneto-resonance absorption signal.

The measuring unit 100 includes a detector 110, a sensor coil 120, a pair of permanent magnets 130, a pair of pole pieces 140, a pair of low frequency coils 150, a pair of acoustic wave coils 160, and a cylindrical shell 170.

The circuit unit 200 includes a high frequency generator 210, a low frequency generator 220, an acoustic wave generator 230, an amplitude detector 240, a preamplifier 250, an acoustic wave amplifier 260, a band pass filter 270, a calculating unit 280, and a drive controller 290.

Figure 6:
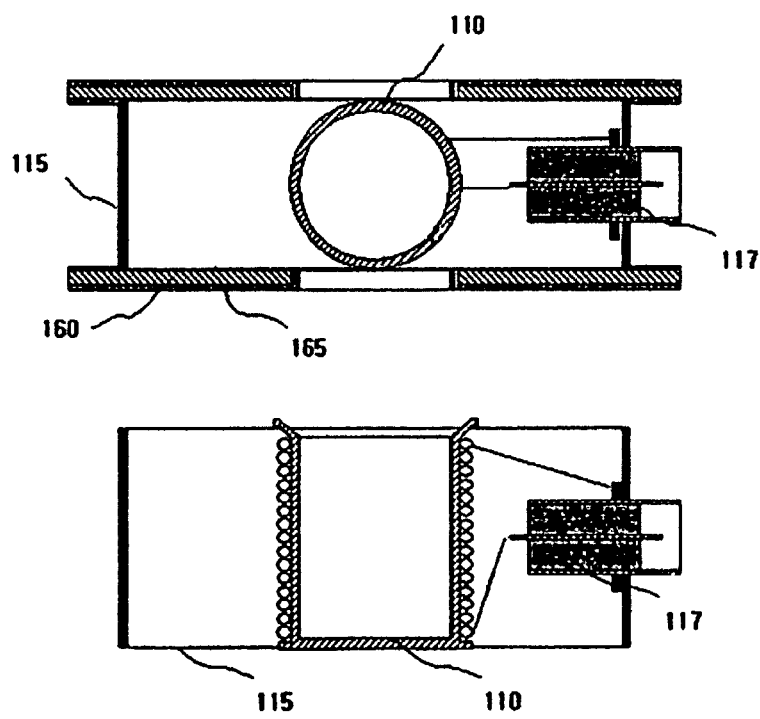
FIG. 6 is a cross-sectional view and a plan view of a detector and coupling elements of the non-invasive blood glucose sensor shown in FIG. 3.

FIG. 6 is a cross-sectional view and a plan view of the detector 110 and coupling elements of the non-invasive blood glucose sensor shown in FIG. 3.

The detector 110 is formed of Teflon in a cylindrical shape having a diameter of about 15 mm, a height of about 20 mm, and a stopped side so as to fix the finger.

The sensor coil 120 is wound in a circumferential direction of the detector 110 and a quality factor thereof is about 40. The sensor coil 120 applies electromagnetic waves generated by the high frequency generator 210 to the detector 110 and measures a magneto-resonance absorption signal produced by spin-lattice relaxation of protons.

The detector 110 around which the sensor coil 120 is wound is installed in the center of a shield 115 formed of a brass material. A high frequency plug 117 electrically coupling the sensor coil 120 and the high frequency generator 210 is installed at a side of the shield 115.

The pair of permanent magnets 130 are formed of a rare-earth material such as NdFeB, SmCo, or the like in a cylindrical shape. An air gap, which includes the shield 115, the pair of acoustic wave coils 160, and the pair of pole pieces 140, is formed between the pair of permanent magnets 130 so that opposite magnetic poles face each other. A constant magnetic field formed in the detector 110 by the pair of permanent magnets 130 has a strength within a range between 0.15 T and 0.35 T.

The pair of pole pieces 140 are formed of an alloy of Fe and Co in a circular plate shape and disposed inside the pair of permanent magnets 130 so as to improve the uniformity of the constant magnetic field in the detector 110. The pair of pole pieces 140 are disposed so that a rotation axis thereof coincides with a rotation axis of the pair of permanent magnets 130. A diameter and the shape of the pair of pole pieces 140 are adjusted so as to improve the uniformity of the constant magnetic field in the detector 110. For reference, in the present invention, the constant magnetic field can have a uniformity within a range of ±0.6 G using the pair of pole pieces 140.

The pair of low frequency coils 150 are wound around the pair of permanent magnets 130 in a circumferential direction of the pair of permanent magnets 130 and are electrically coupled to the low frequency generator 220 to apply a low frequency modulation magnetic field having an amplitude within a range between 0.0003 T and 0.001 T and a cycle at least about 10 times a detected magneto-resonance spin-lattice relaxation time to the detector 110.

The pair of acoustic wave coils 160 are wound inside frames 165 installed at an outer side of the shield 115 in a circumferential direction of the pair of pole pieces 140. The frames 165 contact the pair of pole pieces 140. The pair of acoustic wave coils 160 are electrically coupled to the acoustic wave generator 230 and applies an acoustic wave modulation magnetic field having an amplitude of about 0.5 G and being modulated into an acoustic frequency of about 2 KHz or 5 KHz to the detector 110. Thus, SNRs of pairs of absorption pulses of a weak magneto-resonance absorption signal can be improved due to nuclear magneto-resonance so as to detect the pairs of absorption pulses.

The cylindrical shell 170 is formed in a cylindrical structure to have the same rotation axis as the detector 110 so as to form a magnetic circuit together with the above-described elements. The cylindrical shell 170 limits a distribution of a magnetic field inside, reduces the dispersion of the magnetic field to the outside, and is insensitive to an external magnetic field.

Upper and lower protection plates 172 and 174 are formed of a plastic material in a circular shape on and beneath the cylindrical shell 170 to protect internal elements. An insertion hole 176 through which a finger is inserted is formed in the center of the upper protection plate 172, and a hole 178 is formed in the center of the lower protection plate 174 to electrically couple internal coils to the circuit unit 200.

The high frequency generator 210 is electrically coupled to the sensor coil 120 and is a kind of positive feedback amplifier which generates electromagnetic waves having a small amplitude, the electromagnetic waves corresponding to a magneto-resonance frequency of protons for producing nuclear magneto-resonance, and which measures a magneto-resonance absorption signal produced by spin-lattice relaxation of the protons.

The low frequency generator 220 is electrically coupled to the pair of low frequency coils 150 and generates the electromagnetic waves for applying the low frequency modulation magnetic field having the amplitude within the range between 0.0003 T and 0.001 T and the cycle at least about 10 times the detected magneto-resonance spin-lattice relaxation time to the detector 110.

The acoustic wave generator 230 is electrically coupled to the pair of acoustic wave coils 160 and generates the electromagnetic waves for applying the acoustic wave modulation magnetic field having the amplitude of about 0.5 G and being modulated into the acoustic frequency of about 2 KHz or 5 KHz to the detector 110.

The reduction in the quality factor of the drive circuit of the high frequency generator 210 is caused by electromagnetic energy loss during realizing of resonance conditions in the sensor coil 120. Such variations in a magnetic induction characteristic or a capacity characteristic cause variations in a resonance frequency. A finger positioned in the detector 110 varies a frequency generated by the high frequency generator 210 up to several percent. To remove such a phenomenon, the amplitude of the absorption signal detected by the amplitude detector 240 is transmitted to the drive controller 290 so that the drive controller 290 controls the frequency generated by the high frequency generator 210, so as to automatically tune the frequency via the high frequency generator 210. An amplitude stabilizer 245 is additionally provided to maintain a value of the amplitude of the absorption signal detected by the amplitude detector 240 for a predetermined period of time so as to stably transmit the value of the amplitude to the drive controller 290.

The preamplifier 250 amplifies the absorption signal having passed through the amplitude detector 240 in a high frequency band.

The acoustic wave amplifier 260 and the band pass filter 270 amplify and select only components of the absorption signal amplified by the preamplifier 250 in an acoustic frequency band. As a result, an SNR can be improved to improve measurement precision of blood glucose.

The calculating unit 280 detects amplitudes and time differences of pairs of absorption pulses of the magneto-resonance absorption signal obtained by the band pass filter 270, digitalizes the amplitudes and the time differences via an analog-to-digital converter (ADC), stores the digitalized amplitudes and time differences, and determines the spin-lattice relaxation time of the protons in the finger tissue and the blood glucose concentration in the human body from the amplitudes and the time differences. The calculating unit 280 is embodied as a program in an additional internal microprocessor of the circuit unit or in a personal computer. In particular, if the calculating unit 280 is embodied as the microprocessor, the calculating unit 280 may include an additional pulse measurer and an memory to detect the amplitudes and the time differences of the pairs of absorption pulses of the magneto-resonance absorption signal, digitalize the amplitudes and the time differences via the ADC, and store the amplitudes and the time differences.

The drive controller 290 controls amplitudes and cycles of the electromagnetic waves generated by the high frequency generator 210, the low frequency generator 220, and the acoustic wave generator 230. A power source 295 supplies a power to components of the circuit unit.

Figure 7:
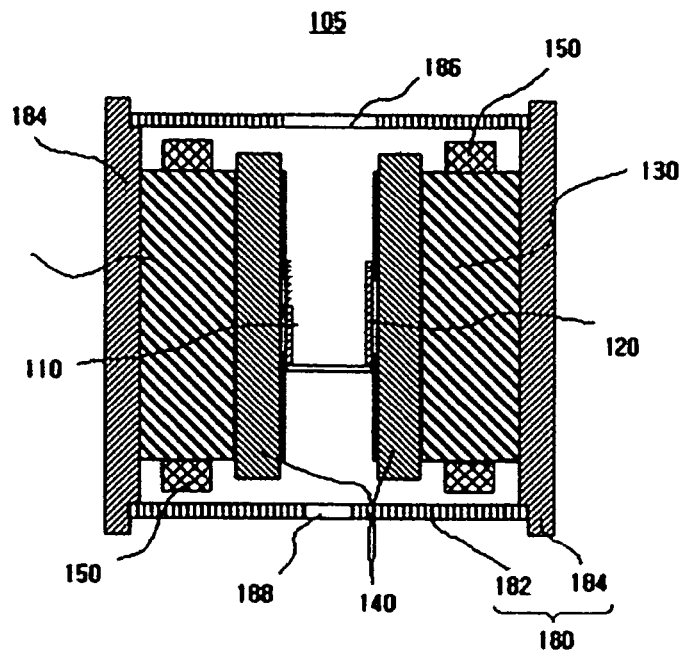
FIG. 7 is a vertical cross-sectional view of a measuring unit of a non-invasive blood glucose sensor using a magneto-resonance absorption method according to another embodiment of the present invention.

FIG. 7 is a vertical cross-sectional view of a measuring unit of a non-invasive blood glucose sensor using a magneto-resonance absorption method according to another embodiment of the present invention. A shell 180 includes a cylinder part 182 having both ends opened so as to easily assemble, disassemble, arrange, and rearrange elements in the measuring unit 100 and a pair of plungers 184. An insertion hole 186 through which a finger is inserted and a hole 188 electrically coupling the internal coils to the circuit unit are formed in the center of the cylinder part 182. The pair of plungers 184 are disposed so as to contact outer sides of the pair of permanent magnets 130 and the both ends of the cylinder part 182.

Non-invasive blood glucose measurement methods using a magneto-resonance absorption method according to embodiments of the present invention will now be described.

Figure 8:
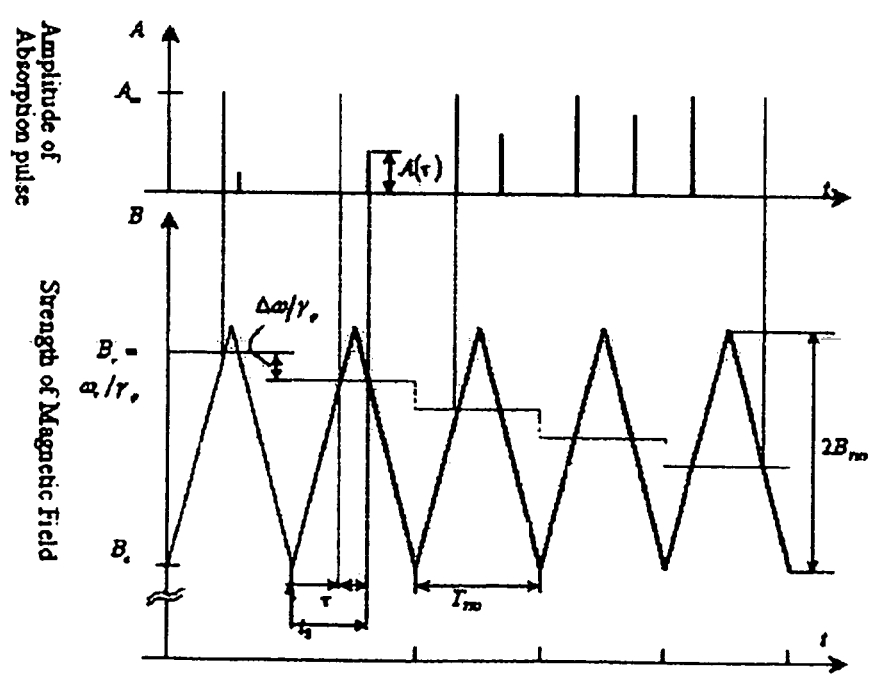
FIG. 8 is a view illustrating a method of forming nuclear magneto-resonance conditions adopting a non-invasive blood glucose measurement method using a magneto-resonance resonance absorption method according to an embodiment of the present invention.

FIG. 8 is a view illustrating a method of forming nuclear magneto-resonance conditions adopting a non-invasive blood glucose measurement method using a magneto-resonance absorption method according to an embodiment of the present invention. In the non-invasive blood glucose measurement method, the pair of permanent magnets 130 apply a constant magnetic field having a uniform strength $B_{TRI}$ to the detector 110, and the low frequency generator 220 and the pair of low frequency coils 150 apply a triangular waveform low frequency modulation magnetic field having a uniform strength $B_{TRI}$ and a cycle $T_{TRI}$ to the detector 110. The pair of acoustic wave coils 160 and the acoustic wave generator 230 apply an acoustic wave modulation magnetic field having a weak strength to the detector 110. The high frequency generator 210 and the sensor coil 120 apply electromagnetic waves sequentially varying by a frequency of $\Delta f$ within a specific frequency range to the detector 110. The drive controller 290 synchronizes the frequency of the electromagnetic waves applied by the high frequency generator 210 with the strength of the triangular waveform low frequency modulation magnetic field so that the frequency of the electromagnetic waves varies when the strength of the triangular waveform low frequency modulation magnetic field is minimum.

As shown in FIG. 8, when electromagnetic waves having a frequency expressed as in Equation 2 are applied to the protons in the tissue of the finger positioned in the detector 110 to which the constant magnetic field $B_C$ and the triangular waveform low frequency modulation magnetic field having the amplitude $B_{TRI}$ and the cycle $T_{TRI}$ are applied, nuclear magneto-resonance occurs two times and a pair of absorption pulses are recorded by spin-lattice relaxation:

$$f_r = \frac{\gamma_p B_r}{2\pi} = \frac{\gamma_p}{2\pi}\left[B_c + \frac{4t_1}{T_{TRI}}B_{TRI}\right] \quad (2)$$

wherein $t_1$ and $t_2$ denote times from when the strength of the triangular waveform low frequency modulation magnetic field is minimum to when first absorption pulses $A\infty$ and second absorption pulses $A(\tau)$ are detected, and $\tau$ denotes a time difference between the times when the first and second pulses $A\infty$ and $A(\tau)$ are detected. In other words, the time $t_1$ is shorter than half of the cycle of the triangular waveform low frequency modulation magnetic field, i.e., $T_{TRI}/2$. In other words, the frequency $f_r$ of the electromagnetic waves applied by the high frequency generator 210 varies by $\Delta f$ step by step within a range between $\gamma_p(B_C-B_{TRI})/2\pi$ and $\gamma_p(B_C+B_{TRI})/2\pi$.

Also, as shown in FIG. 8, the cycle $T_{TRI}$ of the triangular waveform low frequency modulation magnetic field is sufficiently greater than the spin-lattice relaxation time $T_1$ of the finger, i.e., more than 10 times the spin-lattice relaxation time $T_1$ so that the amplitude $A\infty$ of the detected first absorption pulses is constantly uniform. The time difference $\tau$ between the pair of absorption pulses is not greater than the spin-lattice relaxation time $T_1$ of the finger so that the amplitude $A(\tau)$ of the detected second absorption pulses is not greater than the amplitude $A\infty$ of the detected first absorption pulses.

Figure 9:
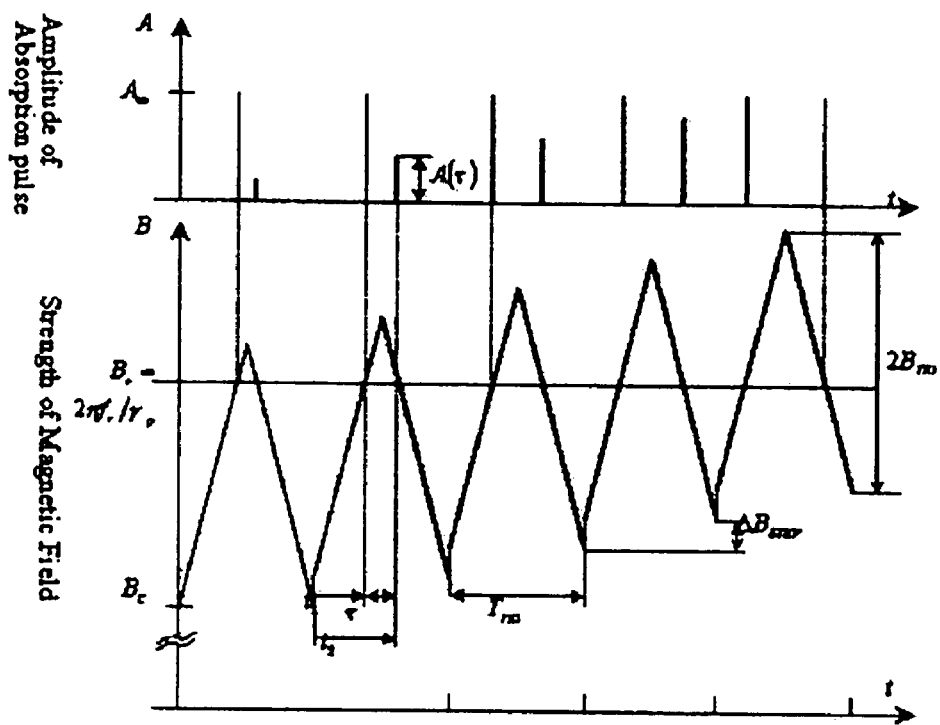
FIG. 9 is a view illustrating a method of forming nuclear magneto-resonance conditions adopting a non-invasive blood glucose measurement method using a magneto-resonance resonance absorption method according to another embodiment of the present invention.

FIG. 9 is a view illustrating a method of forming nuclear magneto-resonance conditions adopting a non-invasive blood glucose measurement method using a magneto-resonance absorption method according to another embodiment of the present invention. In the non-invasive blood glucose measurement method, the low frequency generator 220 and the pair of low frequency coils 150 apply an asymmetric triangular waveform low frequency modulation magnetic field in which modulation of a triangular waveform having a uniform strength is performed and step-by-step modulation is performed at a uniform strength.

As shown in FIG. 9, $2B_{TRI}$ and $T_{TRI}$ denote a strength two times a strength of a triangular waveform of the asymmetric triangular waveform low frequency modulation magnetic field and a cycle of the asymmetric triangular waveform low frequency modulation magnetic field, $\Delta B_{STEP}$ denotes a strength of the asymmetric triangular wave form low frequency modulation magnetic field varying step by step, and $T_{STEP}$ denotes a cycle of the asymmetric triangular wave form low frequency modulation magnetic field which is integer times a cycle of the modulation of the triangular waveform. As a preferred aspect of the present invention, $T_{STEP}$ is four times $T_{TRI}$. Also, $f_r$ denotes the frequency of the electromagnetic waves generated by the high frequency generator 210 and applied to the detector 110 via the sensor coil 120, $\gamma_p$ denotes the gyromagnetic ratio of the protons, $B_r$ denotes the strength of the whole magnetic field during nuclear magneto-resonance, and $B_C$ denotes the strength of the constant magnetic field generated by the pair of permanent magnets 130.

When electromagnetic waves of a uniform resonance frequency $\omega_r$, are applied to the detector 110 under the constant magnetic field having the strength $B_C$, the triangular waveform having the strength $B_{TRI}$, and the asymmetric triangular waveform low frequency modulation magnetic field varying step by step at the strength $\Delta B_{STEP}$, a pair of absorption pulses are recorded in a nuclear magneto-resonance absorption signal detected under the resonance conditions as in Equation 3 in every cycle $T_{TRI}$ of the asymmetric triangular waveform low frequency modulation magnetic field:

$$B_r = \frac{2\pi f_r}{\gamma_p} = B_c + n\Delta B_{step} + \frac{4t_1}{T_{TRI}} B_{TRI} \tag{3}$$

wherein $t_1$ and $t_2$ denote times from when a cycle of the asymmetric triangular waveform low frequency modulation magnetic field starts to when first absorption pulses $A\infty$ and second absorption pulses $A(\tau)$ are detected, $\tau$ denotes a time difference between the times when the first and second pulses $A\infty$ and $A(\tau)$ are detected, and n denotes a number of control pulses applied to the low frequency generator 220 via the drive controller 290. Additional magnetic field modulation is performed together with the acoustic wave coils 160 and the acoustic wave generator 230.

The cycle $T_{TRI}$ of the triangular waveform is sufficiently greater than, i.e., at least more than ten times, the spin-lattice relaxation time $T_1$ of the finger so that the amplitude $A\infty$ of the first absorption pulses detected during the modulation of the asymmetric low frequency magnetic field is constantly uniform. Also, the time difference $\tau$ between the pair of absorption pulses is not greater than the spin-lattice relaxation time $T_1$ of the finger so that the amplitude $A(\tau)$ of the second absorption pulses is not greater than the amplitude $A\infty$ of the first absorption pulses.

Figure 10:
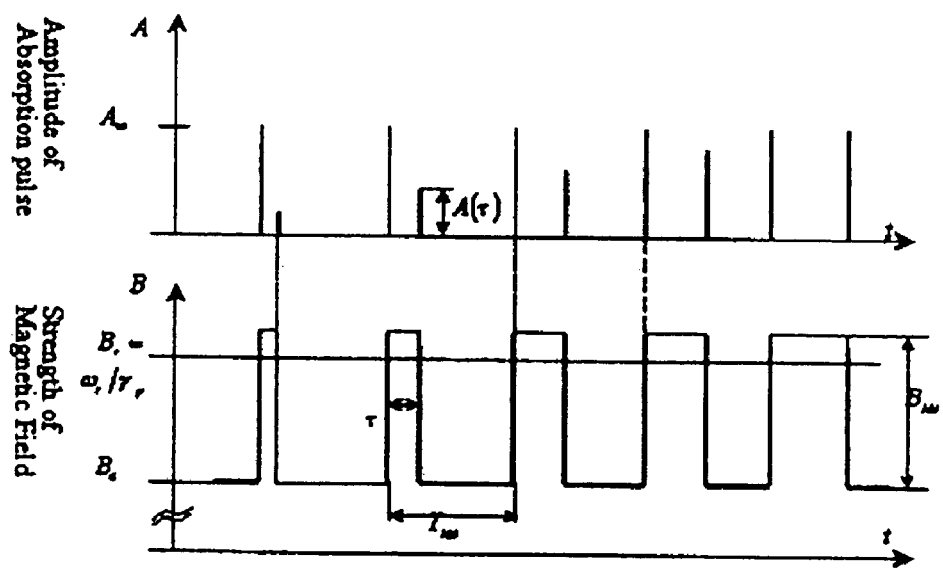
FIG. 10 is a view illustrating a method of forming nuclear magneto-resonance conditions adopting a non-invasive blood glucose measurement method using a magneto-resonance absorption method according to still another embodiment of the present invention.

FIG. 10 is a view illustrating a method of forming nuclear magneto-resonance conditions adopting a non-invasive blood glucose measurement method using a magneto-resonance absorption method according to still another embodiment of the present invention. The low frequency generator 220 and the pair of low frequency coils 150 apply the constant magnetic field of the strength $B_C$ generated by the pair of permanent magnets 130 and an impulse form low frequency modulation magnetic field having a strength BIM and a cycle TIM to the detector 110, and the high frequency generator 210 and the sensor coil 120 apply the electromagnetic waves of the uniform resonance frequency $\omega_r$ to the detector 110, nuclear magneto-resonance occurs one time whenever the impulse ascends and descends. In other words, the strength $B_{IM}$ of the impulse form low frequency modulation magnetic field is greater than a difference between the strength Br of the resonance frequency and the strength Bc of the constant magnetic field as in Equation 4 so as to detect a pair of absorption pulses in every cycle of low frequency modulation.

$$B_{IM} > B_r - B_C = \omega_r/\gamma_p - B_C \tag{4}$$

Also, the cycle $T_{IM}$ of the impulse form low frequency modulation magnetic field is at least more than ten times the spin-lattice relaxation time $T_1$ of the finger so that the amplitude $A\infty$ of the first absorption pulses detected when the impulse ascends is constantly uniform. A lasting time $\tau$ of an impulse wave is shorter than the spin-lattice relaxation time $T_1$ of the finger and increases in each cycle so that the amplitude $A(\tau)$ of the second absorption pulses detected when the impulse descends is not greater than the amplitude $A\infty$ of the first absorption pulses.

In the above-described non-invasive blood glucose measurement methods according to the present invention, a nuclear magneto-resonance absorption signal passes through the amplitude measurer 240, the preamplifier 250, the acoustic wave amplifier 260, and the band pass filter 270 so as to detect acoustic frequency band components via the high frequency generator 210. Thereafter, the calculating unit 280 converts amplitudes and time differences of pairs of nuclear magneto-resonance absorption pulses into digital values via the ABC and stores the digital values.

Figure 11:
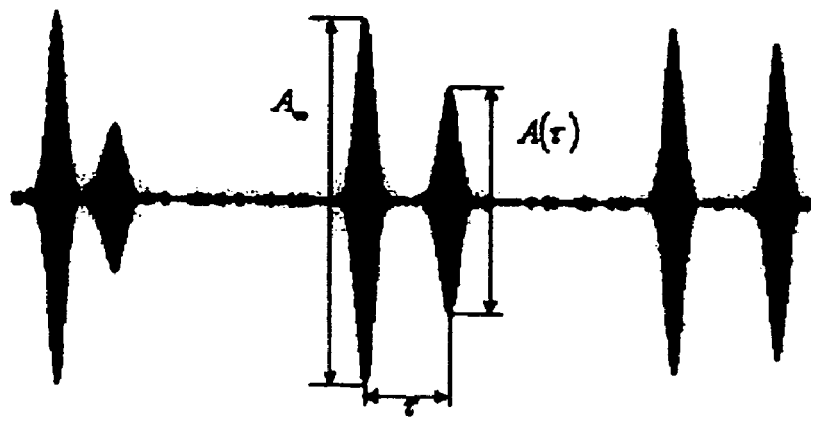
FIG. 11 is a view illustrating pairs of continuous absorption pulses of a nuclear magneto-resonance absorption signal detected via non-invasive blood glucose sensors and methods according to the present invention.

FIG. 11 is a view illustrating pairs of continuous absorption pulses of a nuclear magneto-resonance absorption signal detected via non-invasive blood glucose sensors and methods according to the present invention. Compared to the nuclear magneto-resonance absorption signal detected via the conventional non-invasive blood glucose sensor as shown in FIG. 2, the nuclear magneto-resonance absorption signal detected via the non-invasive blood glucose sensor according to the present invention includes low noise components. In this case, an SNR is about 64, i.e., about six times an SNR according to the prior art. Thus, the uniformity of the external magnetic field in the detector 110 is improved using the pair of pole pieces 140. The amplitudes and the time differences of the pairs of absorption pulses of the nuclear magneto-resonance absorption signal shown in FIG. 11 are stored in the calculating unit 280.

Figure 12:
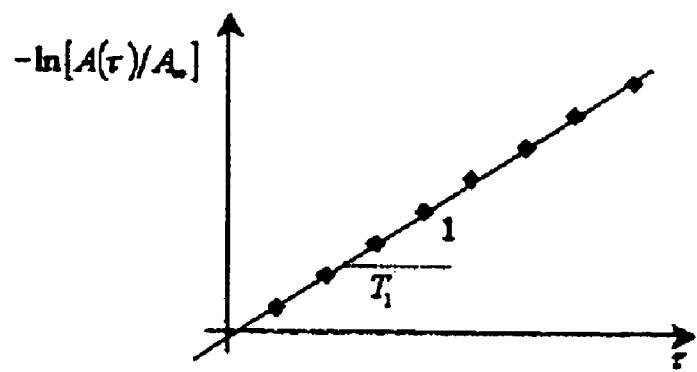
FIG. 12 is a graph illustrating a determination of a spin-lattice relaxation time of a finger tissue from a nuclear magneto-resonance absorption signal.

The calculating unit 280 determines the spin-lattice relaxation time of the tissue of the finger and the blood glucose concentration in the human body from the amplitudes and the time differences of the pairs of absorption pulses. FIG. 12 is a graph illustrating a determination of a spin-lattice relaxation time of a finger tissue from a nuclear magneto-resonance absorption signal. Referring to FIG. 12, $\tau$ denotes a difference between times when a pair of absorption pulses are generated in every cycle of a low frequency modulation magnetic field, $A\infty$ denotes amplitude of first absorption pulses, and $A(\tau)$ denotes amplitude of second absorption pulses. The nuclear magneto-resonance spin-lattice relaxation time $T_1$ of the finger tissue is expressed as an inverse number of a straight inclination shown in FIG. 12 as in Equation 5:

$$T_1 = \frac{\tau}{-\ln\left[1 - \frac{A(\tau)}{A\infty}\right]} \tag{5}$$

According to Equation 5, the spin-lattice relaxation time of the finger tissue is determined. Thereafter, a blood glucose concentration in the human body is determined from the spin-lattice relaxation time of the finger tissue determined using a correlation between the blood glucose concentration in the human body and the nuclear magneto-resonance spin-lattice relaxation time of the finger tissue stored in the calculating unit 280. A user pre-determines the correlation through several-time measurement at a preliminary stage prior to substantial measurement so as to pre-store the correlation in the calculating unit 280.

The determined blood glucose concentration is displayed on an additional display of the circuit unit 200 or on a program of a personal computer to be offered to the user.

As described above, in a non-invasive blood glucose sensor and method using a magneto-resonance absorption method according to the present invention, the non-invasive blood glucose sensor can be easily used and have size and weight suitable for use. Also The non-invasive blood glucose sensor can secure the desired uniformity of a magnetic field. As a result, non-invasive blood glucose sensor can be used in homes.

Also, diabetics can perform periodic self-measurement non-invasively, that is, without having to prick their fingers or the like for blood sample. Thus, diabetes can be easily managed.

In addition, additional cost is not required for diagnostic strips, diagnostic reagents, or the like. Therefore, the diabetics and the family can relieve economic burden.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A non-invasive blood glucose sensor using a magneto-resonance absorption method, comprising:
   a measuring unit operable to form a plurality of magnetic fields, the plurality of magnetic fields operable to measure a spin-lattice relaxation time of protons in a tissue of a finger, the measuring unit further operable to apply electromagnetic waves and use a magneto-resonance method to detect a nuclear magneto-resonance-absorption signal; and
   a circuit unit operable to generate the electromagnetic waves and determine the spin-lattice relaxation time, the circuit unit further operable to determine a blood glucose concentration in a human body based on the nuclear magneto-resonance absorption signal,
   wherein the measuring unit comprise:
   a detector which is sized to accept and fix a single finger to measure the spin-lattice relaxation time;
   a sensor coil operable to apply electromagnetic waves to the detector and measure the nuclear magneto-resonance absorption signal, the electromagnetic waves having a frequency adapted to produce a nuclear magneto-resonance;
   a pair of permanent magnets operable to apply a uniform constant magnetic field to the detector;
   a pair of pole pieces operable to improve a uniformity of the constant magnetic field;
   a pair of low frequency coils wound around the permanent magnets and operable to apply a low frequency modulation magnetic field to the detector;
   a shield in which the detector and the sensor coil are embodied, which shield couples the detector and the sensor coil to the pole pieces;
   a pair of acoustic waves coils operable to apply an acoustic wave modulation magnetic field to the detector to detect a weak absorption signal, the acoustic magnetic coils being disposed at an outer side of the shield; and
   a cylindrical shell operable to couple internal elements to form a magnetic circuit and performing magnetic shielding.

2. The non-invasive blood glucose sensor of claim 1, wherein sensor coil has a cylindrical shape, a side of which is wound in circumferential direction of the detector.

3. The non-invasive blood glucose sensor of claim 1, wherein the pair of permanent magnets are formed of a rare-earth material.

4. The non-invasive blood glucose sensor of claim 3, wherein the rare-earth material is NdFeB or SmCo.

5. The non-invasive blood glucose sensor of claim 1, wherein the pair of permanent magnets and the pair of pole pieces are circular, have a same rotation axes, and are disposed perpendicular to a rotation axis of the sensor coil.

6. The non-invasive blood glucose sensor of claim 1, wherein the shell is cylindrical and comprises a rotation axis coinciding with a rotation axis of the detector, the shell having both ends opened, and the shell having an inner wall with a portion protruding inside, the protruding portion disposed to be coupled to the pair of permanent magnets.

7. The non-invasive blood glucose sensor of claim 6, wherein an upper circular protection plate and a lower protection plate are attached to the both ends of the shell to protect inner elements.

8. The non-invasive blood glucose sensor of claim 7, wherein an insertion hole operable to have a finger inserted into the shell is provided in a center of the upper circular protection plate and a hole operable to electrically couple the inner elements is provided in a center of the lower circular protection plate.

9. The non-invasive blood glucose sensor of claim 1, wherein the cylindrical shell has a same rotation axis as the rotation axes of the pair of permanent magnets and the pair of pole pieces and a pair of plungers disposed at outer sides of the pair of permanent magnets.

10. The non-invasive blood glucose sensor of claim 9, wherein an insertion hole through which a finger is inserted into the cylindrical shell and a hole electrically coupling the internal elements are formed in a center of the cylinder shell.

11. The non-invasive blood glucose sensor of claim 1, wherein the circuit unit comprises:
    a high frequency generator operable to generate electromagnetic waves having a frequency adapted to produce a nuclear magneto-resonance and detect a magneto-resonance absorption signal;
    a low frequency generator operable to generate electromagnetic waves adapted to apply a low frequency modulation magnetic field to the detector;
    an acoustic wave generator operable to generate acoustic waves adapted to apply an acoustic wave modulation magnetic field to the detector;
    an amplitude detector operable to measure an amplitude of the detected weak absorption signal;
    a preamplifier operable to amplify the weak absorption signal;
    an acoustic wave amplifier operable to amplify an acoustic wave band component of the absorption signal;
    a band pass filter operable to selectively detect the acoustic wave band component of the absorption signal;
    a calculating unit operable to determine the spin-lattice relaxation time and the blood glucose concentration based on the absorption signal; and
    a drive controller controlling operations of various elements in the sensor.

12. The non-invasive blood glucose sensor of claim 11, wherein the circuit unit further comprises:
    an amplitude stabilizer operable to stabilize the amplitude and further operable to transmit the stabilized amplitude to the drive controller.

13. The non-invasive blood glucose sensor of claim 11, wherein the circuit unit further comprises:
    a gain controller operable to control a gain of the band pass filter.

14. The non-invasive blood glucose sensor of claim 11, wherein the circuit unit further comprises:

a display operable to display the blood glucose concentration determined by the calculating unit.

15. The non-invasive blood glucose sensor of a claim 1, wherein the sensor coil has a cylinder shape, a side of which is able to fix the finger being measured.

16. The non-invasive glucose sensor of claim 1, wherein the absorption signal is produced by spin-lattice relaxation in a tissue.

17. A non-invasive blood glucose measurement method using a magneto-resonance absorption method and a non-invasive blood glucose sensor comprising:
a measuring unit operable to form a plurality of magnetic fields, the plurality of magnetic fields operable to enable measurement of a spin-lattice relaxation time of protons in a tissue of a finger, the measuring unit further operable to apply electromagnetic waves and use a magneto-resonance method to detect a nuclear magneto-resonance absorption signal; and
a circuit unit operable to generate the electromagnetic waves and determine the spin-lattice relaxation time, the circuit unit further operable to determine a blood glucose concentration in a human body based on the nuclear magneto-resonance absorption signal,
wherein the measuring unit comprises:
a detector which is sized to accept and fix a single finger to measure the spin-lattice relaxation time;
a sensor coil operable to apply electromagnetic waves to the detector and measure the nuclear magneto-resonance absorption signal, the electromagnetic waves having a frequency adapted to produce a nuclear magneto-resonance;
a pair of permanent magnets operable to apply a uniform constant magnetic field to the detector;
a pair of pole pieces operable to improve a uniformity of the constant magnetic field;
a pair of low frequency coils wound around the permanent magnets and operable to apply a low frequency modulation magnetic field to the detector;
a shield in which the detector and the sensor coil are embodied, which shield couples the detector and the sensor coil to the pole pieces;
a pair of acoustic wave coils operable to apply an acoustic wave modulation magnetic field to the detector to detect a weak absorption signal, the acoustic magnetic coils being disposed at an outer side of the shield; and
a cylindrical shell operable to couple internal elements to form a magnetic circuit and performing magnetic shielding,
the method comprising:
applying a constant magnetic field using the pair of permanent magnets, the magnetic field having a uniform strength;
applying a triangular waveform low frequency modulation magnetic field using a low frequency generator and the pair of low frequency coils, the low frequency modulation magnetic field having a uniform strength;
applying a weak acoustic wave modulation magnetic field using an acoustic wave generator and the pair of acoustic wave coils;
applying electromagnetic waves to the detector in which the finger is positioned to produce the nuclear magneto-resonance, the electromagnetic waves having a frequency varying in a specific frequency band step by step, the applying being done using a high frequency generator and the sensor coil;
detecting a magneto-resonance absorption signal produced by spin-lattice relaxation of protons in a tissue of the finger because of the nuclear magneto-resonance;
determining a magneto-resonance spin-lattice relaxation time of the finger from the magneto-resonance absorption signal; and
determining a blood glucose concentration in a human body from a correlation between a pre-determined blood glucose concentration in the human body and the determined magneto-resonance spin-lattice relaxation time.

18. The non-invasive blood glucose measurement method of claim 17, wherein the triangular waveform low frequency modulation magnetic field has a cycle at least more than ten times the magneto-resonance spin-lattice relaxation time.

19. The non-invasive blood glucose measurement method of claim 17, wherein a time when the frequency of the electromagnetic waves varies step by step is synchronized with a time when a strength of the triangular waveform low frequency modulation magnetic field is minimum.

20. The non-invasive blood glucose measurement method of claim 17, wherein absorption pulses of the nuclear magneto-resonance absorption signal are recorded two times in each cycle of the triangular waveform low frequency modulation magnetic field, differences of time when two absorption pulses are recorded vary with the step-by-step variations in the frequency of the electromagnetic waves, and the cycle is divided depending on each of the time differences.

21. The non-invasive blood glucose measurement method of claim 17, wherein the detection of the magneto-resonance absorption signal comprises:
automatically varying a magneto-resonance frequency based on amplitudes of absorption pulses detected by an amplitude detector.

22. The non-invasive blood glucose measurement method of claim 17, wherein the detection of the magneto-resonance absorption signal further comprises:
amplifying a weak absorption signal via a preamplifier;
amplifying an acoustic wave band component via an acoustic wave amplifier; and
selectively detecting only the acoustic wave band component.

23. A non-invasive blood glucose measurement method using a magneto-resonance absorption method and a non-invasive blood glucose sensor comprising:
a measuring unit operable to form a plurality of magnetic fields, the plurality of magnetic fields operable to enable measurement of a spin-lattice relaxation time of protons in a tissue of a finger, the measuring unit further operable to apply electromagnetic waves and use a magneto-resonance method to detect a nuclear magneto-resonance absorption signal; and
a circuit unit operable to generate the electromagnetic waves and determine the spin-lattice relaxation time, the circuit unit further operable to determine a blood glucose concentration in a human body based on the nuclear magneto-resonance absorption signal,
wherein the measuring unit comprises:
a detector which is sized to accept and fix a single finger to measure the spin-lattice relaxation time:
a sensor coil operable to apply electromagnetic waves to the detector and measure the nuclear magneto-resonance absorption signal, the electromagnetic waves having a frequency adapted to produce a nuclear magneto-resonance;
a pair of permanent magnets operable to apply a uniform constant magnetic field to the detector;

a pair of pole pieces operable to improve a uniformity of the constant magnetic field;

a pair of low frequency coils wound around the permanent magnets and operable to apply a low frequency modulation magnetic field to the detector;

a shield in which the detector and the sensor coil are embodied, which shield couples the detector and the sensor coil to the pole pieces;

a pair of acoustic wave coils operable to apply an acoustic wave modulation magnetic field to the detector to detect a weak absorption signal, the acoustic magnetic coils being disposed at an outer side of the shield; and a cylindrical shell operable to couple internal elements to form a magnetic circuit and performing magnetic shielding, the method comprising:

applying a constant magnetic field having a uniform strength using the pair of permanent magnets;

applying a triangular waveform using a low frequency generator and the pair of low frequency coils, the triangular waveform having a uniform strength and an asymmetric low frequency modulation magnetic field increasing step by step at a uniform strength;

applying a weak acoustic wave modulation magnetic field using an acoustic wave generator and the pair of acoustic wave coils;

applying electromagnetic waves having a uniform resonance frequency to the detector in which the finger is positioned to produce a nuclear magneto-resonance, the applying being done using a high frequency generator and the sensor coil;

detecting a magneto-resonance absorption signal produced by spin-lattice relaxation of protons in a tissue of the finger because of the nuclear magneto-resonance;

determining a magneto-resonance spin-lattice relaxation time of the finger from the magneto-resonance absorption signal; and determining a blood glucose concentration in a human body from a correlation between a pre-determined blood glucose concentration in a human body and the determined magneto-resonance spin-lattice relaxation time.

24. The non-invasive blood glucose measurement method of claim 23, wherein the asymmetric low frequency modulation magnetic field comprises a stepped modulation component varying step by step at a uniform strength interval together with a triangular waveform modulation component having a uniform amplitude approaching a first cycle after some time.

25. The non-invasive blood glucose measurement method of claim 24, wherein a first time when the stepped modulation component varies is synchronized with a second time when the triangular wave form modulation component is minimum.

26. The non-invasive blood glucose measurement method of claim 24, wherein a second cycle of the stepped modulation component is integer times the first.

27. The non-invasive blood glucose measurement method of claim 24, wherein the first cycle is at least more than ten times the spin-lattice relaxation time.

28. The non-invasive blood glucose measurement method of claim 23, wherein absorption pulses of the nuclear magneto-resonance absorption signal are recorded two times in each first cycle, differences of times when two absorption pulses are recorded vary with variations in the stepped modulation component, and the first cycle is divided based on each of the time differences.

29. The non-invasive blood glucose measurement method of claim 23, wherein the detection of the magneto-resonance absorption signal comprises:

automatically varying a magneto-resonance frequency based on amplitudes of absorption pulses detected by an amplitude detector.

30. The non-invasive blood glucose measurement method of claim 23, wherein the detection of the magneto-resonance absorption signal further comprises:

amplifying a weak absorption signal via a preamplifier;

amplifying an acoustic wave band component via an acoustic wave amplifier; and selectively detecting only the acoustic wave band component.

31. A non-invasive blood glucose measurement method using a magneto-resonance absorption method and a non-invasive blood glucose sensor comprising:

a measuring unit operable to form a plurality of magnetic fields, the plurality of magnetic fields operable to enable measurement of a spin-lattice relaxation time of protons in a tissue of a finger, the measuring unit further operable to apply electromagnetic waves and use a magneto-resonance method to detect a nuclear magneto-resonance absorption signal; and a circuit unit operable to generate the electromagnetic waves and determine the spin-lattice relaxation time, the circuit unit further operable to determine a blood glucose concentration in a human body based on the nuclear magneto-resonance absorption signal, wherein the measuring unit comprises:

a detector which is sized to accept and fix a single finger to measure the spin-lattice relaxation time;

a sensor coil operable to apply electromagnetic waves to the detector and measure the nuclear magneto-resonance absorption signal, the electromagnetic waves having a frequency adapted to produce a nuclear magneto-resonance;

a pair of permanent magnets operable to apply a uniform constant magnetic field to the detector;

a pair of pole pieces operable to improve a uniformity of the constant magnetic field;

a pair of low frequency coils wound around the permanent magnets and operable to apply a low frequency modulation magnetic field to the detector;

a shield in which the detector and the sensor coil are embodied, which shield couples the detector and the sensor coil to the pole pieces;

a pair of acoustic wave coils operable to apply an acoustic wave modulation magnetic field to the detector to detect a weak absorption signal, the acoustic magnetic coils being disposed at an outer side of the shield; and a cylindrical shell operable to couple internal elements to form a magnetic circuit and performing magnetic shielding, the method comprising:

applying a constant magnetic field having a uniform strength using the pair of permanent magnets;

applying an impulse form low frequency modulation magnetic field using the low frequency generator and a pair of low frequency coils;

applying an acoustic wave modulation magnetic field using an acoustic wave generator and the pair of acoustic wave coils;

applying electromagnetic waves having a uniform frequency using a high frequency generator and the sensor coil;

detecting a magneto-resonance absorption signal produced by spin-lattice relaxation of protons in a tissue of the finger during the nuclear magneto-resonance;

determining a magneto-resonance spin-lattice relaxation time of the finger from the magneto-resonance absorption signal; and determining a blood glucose concentration in the human body from a correlation between a pre-determined blood glucose concentration in the human body and the determined magneto-resonance spin-lattice relaxation time.

32. The non-invasive blood glucose measurement method of claim 31, wherein a cycle of the impulse form low frequency modulation magnetic field is at least more than ten times the magneto-resonance spin-lattice relaxation time of the protons in the finger tissue.

33. The non-invasive blood glucose measurement method of claim 31, wherein a lasting time of an impulse of the impulse form low frequency modulation magnetic field increases step by step in each of the cycle.

34. The non-invasive blood glucose measurement method of claim 31, wherein an amplitude of the impulse is greater than a difference between a strength of a magnetic field corresponding to a resonance frequency of the electromagnetic waves and a strength of the constant magnetic field, the amplitude being greater to detect a pair of absorption pulses in each of the cycle.

35. The non-invasive blood glucose measurement method of claim 31, wherein the detection of the magneto-resonance absorption signal comprises:

automatically varying a magneto-resonance frequency based on amplitudes of absorption pulses detected by an amplitude detector.

36. The non-invasive blood glucose measurement method of claim 31, wherein the detection of the magneto-resonance absorption signal further comprises:

amplifying a weak absorption signal via a preamplifier;

amplifying an acoustic wave band component via an acoustic wave amplifier; and selectively detecting only the acoustic wave band component.

* * * * *